(12) United States Patent
Nagi et al.

(10) Patent No.: US 8,664,208 B2
(45) Date of Patent: *Mar. 4, 2014

(54) TANAPROGET COMPOSITIONS CONTAINING ETHINYL ESTRADIOL

(75) Inventors: Arwinder Nagi, Thiells, NY (US); Ramarao Chatlapalli, Hopewell Junction, NY (US); Shamim Hasan, East Elmhurst, NY (US); Zafar Ali, Danbury, CT (US); Mohamed Ghorab, Edison, NJ (US)

(73) Assignee: Wyeth LLC, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/292,405

(22) Filed: Nov. 9, 2011

(65) Prior Publication Data

US 2012/0114748 A1     May 10, 2012

Related U.S. Application Data

(63) Continuation of application No. 11/448,965, filed on Jun. 7, 2006, now abandoned.

(60) Provisional application No. 60/688,806, filed on Jun. 9, 2005.

(51) Int. Cl.
*A61K 31/56*     (2006.01)
*A61K 31/535*     (2006.01)

(52) U.S. Cl.
USPC ........................................ 514/171; 514/230.5

(58) Field of Classification Search
USPC ........................................ 514/170, 171, 230.5
See application file for complete search history.

(56) References Cited

U.S. PATENT DOCUMENTS

| | | | |
|---|---|---|---|
| 6,423,699 | B1 | 7/2002 | Grubb |
| 6,436,929 | B1 | 8/2002 | Zhang |
| 7,759,341 | B2 | 7/2010 | Tesconi |
| 7,767,668 | B2 | 8/2010 | Nagi |
| 7,786,297 | B2 | 8/2010 | Chatlapalli |
| 7,968,709 | B2 | 6/2011 | Tesconi |
| 2003/0092711 | A1 | 5/2003 | Zhang |
| 2004/0006060 | A1 | 1/2004 | Fensome |
| 2004/0014798 | A1 | 1/2004 | Fensome |
| 2006/0009428 | A1 | 1/2006 | Grubb |
| 2006/0035843 | A1 | 2/2006 | Shen |
| 2006/0142280 | A1 | 6/2006 | Zhang |
| 2006/0246128 | A1 | 11/2006 | Nagi |
| 2006/0247234 | A1 | 11/2006 | Nagi |
| 2006/0280800 | A1 | 12/2006 | Nagi |
| 2010/0189789 | A1 | 7/2010 | Nagi |
| 2010/0292198 | A1 | 11/2010 | Grubb |
| 2011/0091539 | A1 | 4/2011 | Nagi |
| 2011/0212953 | A1 | 9/2011 | Tesconi |

FOREIGN PATENT DOCUMENTS

| | | |
|---|---|---|
| WO | WO-00/66570 | 11/2000 |
| WO | WO-04/000230 | 12/2003 |
| WO | WO-04/000801 | 12/2003 |
| WO | WO-2006/014476 | 2/2006 |

OTHER PUBLICATIONS

Remington's Pharmaceutical Sciences, 20th Ed., Limmer et al., Eds., Lippincott Williams & Wilkins, Chapter 38, pp. 706 and 997, Baltimore, MD, 2000.
Charbit, "Methods of Particle Production" in Drugs and the Pharmaceutical Sciences: Supercritical Fluid Technology for Drug Product Development, Eds: York et al., Marcel Dekker, Inc., New York, NY, 2004.
"Yakuzai-Gaku Manual", Nanzando Co., Ltd., Japan, pp. 88, 89, 112, and 113, 1989.
Summons to Oral Proceedings dated Mar. 22, 2012 issued in related European Patent Application No. 06772444.3.
Office Action issued dated Apr. 30, 2012 issued in related Indian Patent Application No. 4622/KOLNP/2007.
Applicant's Response to the Office Action dated Dec. 16, 2011 issued in U.S. Appl. No. 12/772,280.
Office Action dated Mar. 23, 2012 issued in U.S. Appl. No. 12/772,280.
Office Action dated Mar. 13, 2012 issued in Japanese Patent Application No. 2008-515878.
Office Action dated Apr. 13, 2012 issued in Australian Patent Application No. 2006258048.
Fensome, "Synthesis and Structure-Activity Relationship of Novel 6-Aryl-1,4-dihydrobenzo[d][1,3]oxazine-2-thiones as Progesterone Receptor Modulators Leading to the Potent and Selective Nonsteroidal Progesterone Receptor Agonists Tanaproget", Journal of Medicinal Chemistry, 48:5092-5095 (Jul. 12, 2005).
Zhang, "Novel 6-Aryl-1,4-dihydrobenzo[d][1,3]oxazine-2-thiones as Potent, Selective, and Orally Active Nonsteroidal Progesterone Receptor Agonists", Bioorganic & Medicinal Chemistry Letters, 13:1313-1316 (2003).
Winneker, "Nonsteroidal Progesterone Receptor Modulators: Structure Activity Relationships", Seminars in Reproductive Medicine, 23(1):46 (2005).
Bapst, "Clinical Pharmacokinetics of Tanaproget, A Non-Steroidal Progesterone Receptor (PR) Agonist, in Healthy Cycling Women During 28 Days of Administration", American Society for Clinical Pharmacology and Therapeutics, Abstract PI-138, (Feb. 2005), p. 44.

(Continued)

*Primary Examiner* — San-Ming Hui
(74) *Attorney, Agent, or Firm* — Howson & Howson LLP

(57) ABSTRACT

Compositions containing micronized tanaproget, or a pharmaceutically acceptable salt thereof, and ethinyl estradiol and methods of preparing the same are provided. Also provided are kits containing the compositions, methods of contraception and hormone replacement therapy including administering a composition containing micronized tanaproget and ethinyl estradiol.

21 Claims, No Drawings

(56) References Cited

OTHER PUBLICATIONS

Crabtree, "Development of a Mouse Model of Mammary Gland Versus Uterus Tissue Selectivity Using Estrogen- and Progesterone-Regulated Gene Markers", Journal of Steroid Biochemistry & Molecular Biology, 101:11-21 (Sep. 2006; e-published Aug. 22, 2006).
Bapst, "Pharmacokinetics and Safety of Tanaproget, a Nonsteroidal Progesterone Receptor Agonist, in Healthy Women", Contraception, 74:414-418 (Nov. 2006; e-published Sep. 15, 2006).
Bruner-Tran, "Down-Regulation of Endometrial Matrix Metalloproteinase-3 and -7 Expression in Vitro and Therapeutic Regression of Experimental Endometriosis in Vivo by a Novel Nonsteroidal Progesterone Receptor Agonist, Tanaproget", The Journal of Clinical Endocrinology & Metabolism, 91(4): 1554-1560 (Apr. 2006; e-published Jan. 17, 2006).
Rasenack, "Micron-Size Drug Particles, common Novel Micronization Techniques", Pharmaceutical Development and Technology, 9(1): 1-13 (2004).
Remington's Pharmaceutical Sciences, 18$^{th}$ Ed., Gennaro et al., Eds., Philadelphia college of Pharmacy and Sciences, pp. 1319, 1322-1323 (1990).
"Sodium Croscarmellose" from http://web.archive.org/web/20031204033945/http://www.nbent.com/crosscarmellose.htm (Dec. 2003).
Meikle, "Endocrine replacement therapy in clinical practice", Human Press, pp. 484, 485, 487, and 490 (2003).
WHO Drug Information, World Health Organization, Geneva, Switzerland, vol. 18, No. 3 (2004).
Office Action dated Dec. 17, 2009 issued in related U.S. Appl. No. 11/412,022.
Applicants' Response to the Office Action dated Dec. 17, 2009 issued in related U.S. Appl. No. 11/412,022.
Office Action dated Jul. 22, 2010 issued in related U.S. Appl. No. 11/412,022.
Office Action dated Sep. 18, 2009 issued in related U.S. Appl. No. 11/412,014.
Applicants' Response to the Office Action dated Sep. 18, 2009 issued in related U.S. Appl. No. 11/412,014.
Office Action dated Apr. 16, 2010 issued in related U.S. Appl. No. 11/412,014.
Applicants' Response to the Office Action dated Apr. 16, 2010 issued in related U.S. Appl. No. 11/412,014.
Office Action dated Nov. 12, 2008 issued in related U.S. Appl. No. 11/412,016.
Applicants' Response to the Office Action dated Nov. 12, 2008 issued in related U.S. Appl. No. 11/412,016.
Office Action dated Aug. 19, 2009 issued in related U.S. Appl. No. 11/412,016.
Applicants' Response to the Office Action dated Aug. 19, 2009 issued in related U.S. Appl. No. 11/412,016.
Office Action dated Nov. 12, 2008 issued in related U.S. Appl. No. 11/412,015.
Applicants' Response to the Office Action dated Nov. 12, 2008 issued in related U.S. Appl. No. 11/412,015.
Office Action dated Apr. 2, 2009 issued in related U.S. Appl. No. 11/412,015.
Applicants' Response to the Office Action dated Apr. 2, 2009 issued in related U.S. Appl. No. 11/412,015.
Office Action dated Nov. 27, 2009 issued in related U.S. Appl. No. 11/412,015.
Applicants' Response to the Office Action dated Nov. 27, 2009 issued in related U.S. Appl. No. 11/412,015.
Office Action dated Jan. 5, 2011 issued in related U.S. Appl. No. 12/792,978.
Applicant's Response to the Office Action dated Jan. 5, 2011 issued in related U.S. Appl. No. 12/792,978.
Office Action dated Oct. 1, 2008 issued in related U.S. Appl. No. 11/411,523.
Applicants' Response to the Office Action dated Oct. 1, 2008 issued in related U.S. Appl. No. 11/411,523.
Office Action dated Mar. 4, 2009 issued in related U.S. Appl. No. 11/411,523.
Applicants' Response to the Office Action dated Mar. 4, 2009 issued in related U.S. Appl. No. 11/411,523.
Office Action dated Jul. 13, 2010 issued in related U.S. Appl. No. 11/448,965.
Applicants' Response to the Office Action dated Jul. 13, 2010 issued in related U.S. Appl. No. 11/448,965.
Office Action dated Jan. 28, 2011 issued in related U.S. Appl. No. 11/448,965.
Office Action dated Jul. 28, 2008 issued in counterpart European Patent Application No. 06772444.3.
Applicants' Response to the Office Action dated Jul. 28, 2008 issued in counterpart European Patent Application No. 06772444.3.
Office Action dated May 6, 2009 issued in counterpart European Patent Application No. 06772444.3.
Applicants' Response to the Office Action dated May 6, 2009 issued in counterpart European Patent Application No. 06772444.3.
Office Action dated Jul. 29, 2010 issued in counterpart European Patent Application No. 06772444.3.
Applicants' Response to the Office Action dated Jul. 29, 2010 issued in counterpart European Patent Application No. 06772444.3.
Office Action dated Oct. 16, 2009 issued in counterpart Chinese Patent Application No. 200680020195.
Office Action dated Sep. 29, 2011 issued in counterpart Chinese Patent Application No. 200680020195.
Office Action dated Jan. 29, 2010 issued in counterpart Honduran Patent Application No. 2006-20928.
Office Action dated Feb. 3, 2011 issued in counterpart Australian Patent Application No. 2006258048.
First Office Action issued in 2011 in counterpart Mexican Patent Application No. MX/A/2007/015571.
Second Office Action issued in 2011 in counterpart Mexican Patent Application No. MX/A/2007/015571.
Office Action issued in 2010 in counterpart Mexican Patent Application No. MX/A/2007/015571.
International Search Report dated Jan. 9, 2007 issued in related International Patent Application No. PCT/US2006/022150.
Office Action dated Mar. 12, 2009 issued in U.S. Appl. No. 11/174,592.
Applicant's Response to the Office Action dated Mar. 12, 2009 issued in U.S. Appl. No. 11/174,592.
Office Action dated Nov. 5, 2009 issued in U.S. Appl. No. 11/174,592.
Office Action dated Dec. 16, 2011 issued in U.S. Appl. No. 12/772,280.
Yakuzai-gaku Manual (Pharmaceutical Manual), Nanzando Co., Ltd., Japan, pp. 88, 89, 112, and 113 (1989).
"Remington the Science and Practice of Pharmacy, 20$^{th}$ Edition", Limmer, Ed., Lippincott Williams & Wilkins, pp. 706 and 997 (2000).
Charbit, "Methods of Particle Production in Supercritical Fluid Technology for Drug Product Development", York, Ed., vol. 138, Marcel Dekker, Inc., p. 152 (2004).
Moyer, "Novel Nonsteroidal Progesterone Receptor Agonist Shows Promise as a Once-Daily Oral Contraceptive, Presented at ACOG" (May 16, 2005).
Chopra, 228$^{th}$ National Meeting of the American Chemical Society, Philadelphia, PA, Abstract MEDI 178 (2004).
Search Report dated Aug. 2, 2012 and issued in Chinese Patent Application No. 200680020195.X.
English translation of an Office Action dated Aug. 2, 2012 and issued in Chinese Patent Application No. 200680020195.X.
English translation of an Office Action dated Mar. 13, 2012 and issued in Japanese Patent Application No. 2008-515878.
English translation of an Office Action dated Nov. 13, 2012 and issued in Japanese Patent Application No. 2008-515878.
Office Action dated Apr. 30, 2012 and issued in Indian Patent Application No. 4622/KOLNP/2007.
Applicant's Response to the Office Action dated Apr. 30, 2012 issued in Indian Patent Application No. 4622/KOLNP/2007.
Office Action dated Aug. 13, 2012 and issued in Canadian Patent Application No. 2,610,767.

(56) References Cited

OTHER PUBLICATIONS

Applicant's Response to the Office Action dated Feb. 3, 2011 issued in Australian Patent Application No. 2006258048.
Office Action dated Apr. 13, 2012 and issued in Australian Patent Application No. 2006258048.
Correspondence from the agent regarding the issuance of an Office Action on Jul. 12, 2012 in Mexican Patent Application No. MX/A/2007/015571.
Summons to Attend Oral Proceedings dated Mar. 22, 2012 and issued in European Patent Application No. 06772444.3.
Applicant's Response to the Summons to Attend Oral Proceedings dated Mar. 22, 2012 issued in European Patent Application No. 06772444.3.
Communication dated Nov. 13, 2012 and issued in European Patent Application No. 06772444.3.
Applicant's Response to the Communication dated Nov. 13, 2012 and issued in European Patent Application No. 06772444.3.
Examination Report dated Feb. 22, 2013 and issued in counterpart Indian Patent Application No. 4622/KOLNP/2007.
Decision dated Jan. 16, 2013 and issued in European Patent Application No. 06772444.3.

TANAPROGET COMPOSITIONS CONTAINING ETHINYL ESTRADIOL

CROSS-REFERENCE TO RELATED APPLICATIONS

This application is a continuation of U.S. patent application Ser. No. 11/448,965, filed Jun. 7, 2006, which claims the benefit of the priority of U.S. Provisional Patent Application No. 60/688,806, filed Jun. 9, 2005. These priority applications are herein incorporated by reference.

BACKGROUND OF THE INVENTION

Compositions containing tanaproget and ethinyl estradiol are provided.

Progesterone receptor (PR) modulators (natural and synthetic) are known to play an important role in the health of women and are often are used in birth control compositions and for hormone replacement therapy.

Tanaproget, 5-(4,4-dimethyl-2-oxo-1,4-dihydro-2H-3,1-benzoxazin-6-yl)-1H-1-methyl-pyrrole-2-carbonitrile, is a progesterone receptor modulator and is effective in contraception, hormone replacement therapy, and treating carcinomas and adenocarcinomas, dysfunctional bleeding, uterine leiomyomata, endometriosis, and polycystic ovary syndrome.

What is needed are compositions containing tanaproget for contraception and hormone replacement therapy.

SUMMARY OF THE INVENTION

In one aspect, compositions containing micronized tanaproget, or a pharmaceutically acceptable salt thereof, and ethinyl estradiol are provided.

In another aspect, compositions containing micronized tanaproget, or a pharmaceutically acceptable salt thereof, ethinyl estradiol, microcrystalline cellulose, anhydrous lactose, croscarmellose sodium, and magnesium stearate are provided.

In a further aspect, processes for preparing a composition containing micronized tanaproget and ethinyl estradiol are provided.

In yet another aspect, kits containing a composition which contains micronized tanaproget and ethinyl estradiol are provided.

In still a further aspect, methods of contraception are provided and include administering a composition containing micronized tanaproget and ethinyl estradiol to female in need thereof.

In another aspect, methods of hormone replacement therapy are provided and include administering a composition containing micronized tanaproget and ethinyl estradiol to a female in need thereof.

Other aspects and advantages of the invention will be readily apparent from the following detailed description of the invention.

DETAILED DESCRIPTION OF THE INVENTION

Effective pharmaceutical compositions containing micronized tanaproget and ethinyl estradiol are described. The composition can be readily formulated into an oral dosage unit, and is particularly well suited for a directly compressible unit.

Briefly, tanaproget is micronized, desirably under nitrogen and by means of conventional micronizing techniques, for example with a Trost or jet mill, applied to non-micronized tanaproget. One method of preparation of non-micronized tanaproget is described in U.S. Pat. No. 6,436,929, and generally in US Patent Application Publication No. US-2005-0272702-A1, which is hereby incorporated by reference. However, the invention is not limited to the method by which the non-micronized tanaproget is produced.

Micronized tanaproget prepared as described herein typically has a particle size of less than about 20 μm, desirably less than about 15 μm, and more desirably less than about 10 μm. Specifically, 90% of the particles are less than or equal to about 20 μm and 50% are less than or equal to about 15 μm as determined by the Malvern method, which is readily understood by one of skill in the art.

The micronized tanaproget encompasses tautomeric forms of tanaproget and salts derived from pharmaceutically or physiologically acceptable acids, bases, alkali metals and alkaline earth metals. Also provided are derivatives of tanaproget, including, but not limited to, esters, carbamates, sulfates, ethers, oximes, carbonates, and the like.

Physiologically acceptable acids include those derived from inorganic and organic acids. A number of inorganic acids are known in the art and include hydrochloric, hydrobromic, hydroiodic, sulfuric, nitric, and phosphoric acids, among others. Similarly, a variety of organic acids are known in the art and include, without limitation, lactic, formic, acetic, fumaric, citric, propionic, oxalic, succinic, glycolic, glucuronic, maleic, furoic, glutamic, benzoic, anthranilic, salicylic, tartaric, malonic, mallic, phenylacetic, mandelic, embonic, methanesulfonic, ethanesulfonic, panthenoic, benzenesulfonic, toluenesulfonic, stearic, sulfanilic, alginic, and galacturonic acids, among others.

Physiologically acceptable bases include those derived from inorganic and organic bases. A number of inorganic bases are known in the art and include aluminum, calcium, lithium, magnesium, potassium, sodium, and zinc sulfate or phosphate compounds, among others. A number of organic bases are known in the art and include, without limitation, N,N,-dibenzylethylenediamine, chloroprocaine, choline, diethanolamine, ethylenediamine, meglumine, and procaine, among others.

Physiologically acceptable alkali salts and alkaline earth metal salts can include, without limitation, sodium, potassium, calcium and magnesium salts in the form of esters, and carbamates.

These salts, as well as the nonmicronized and micronized tanaproget can be in the form of esters, carbamates and other conventional "pro-drug" forms, which, when administered in such form, convert to the active moiety in vivo. In one embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

Micronized tanaproget discussed herein also encompasses "metabolites" which are unique products formed by processing tanaproget by the cell or patient. Desirably, metabolites are formed in vivo.

In one embodiment, the compositions are prepared by dry mixing micronized tanaproget, based upon the total weight of the unit dose, with the other components of the composition to form a dry granulation.

As referred to herein below, the term "wt/wt" refers to the weight of one component based on the total weight of the composition. Typically, this ratio does not include the weight of the capsule, the weight of any filler utilized in the capsule, and seal coating, if so utilized.

A. The Compositions

The compositions described herein are formulated to provide rapid release of tanaproget and ethinyl estradiol, while simultaneously being stable under conditions of storage. In one embodiment, the composition contains micronized tanaproget and ethinyl estradiol. In another embodiment, the composition contains micronized tanaproget, ethinyl estradiol, microcrystalline cellulose (MCC), anhydrous lactose, croscarmellose sodium, and magnesium stearate.

Suitably, micronized tanaproget is present in the composition in an amount from about 0.01% wt/wt to about 1% wt/wt. In one example, the composition contains micronized tanaproget in an amount of about 0.1% to about 0.6% wt/wt. In a further example, the composition contains micronized tanaproget in an amount of about 0.17% to about 1% wt/wt. In another example, the composition contains tanaproget in an amount of about 0.17% wt/wt. In a further example, the composition contains tanaproget in an amount of about 0.35% wt/wt. In yet another example, the composition contains tanaproget in an amount of about 0.52% wt/wt. This amount may be varied, depending upon the amount of micronized tanaproget to be delivered to a patient. In one embodiment, the compositions contain about 100 to about 300 μg of tanaproget, and desirably, about 100, 200, or 300 μg of tanaproget.

Typically, an excess of tanaproget is utilized, and desirably a 5% excess, over the amount of tanaproget that is required for the composition. In another embodiment, when the compositions contain an excess of tanaproget, the compositions contain about 105 to about 315 μg of tanaproget, and desirably about 105, 210, and 315 μg of tanaproget.

Ethinyl estradiol is also present in the compositions described herein. Ethinyl estradiol can be added to the composition as an individual component or can be added with one or more excipients. In one example, ethinyl estradiol is added to the composition as an individual component and includes about 0.03 to about 0.05% wt/wt of the composition. In another example, ethinyl estradiol is added to the composition as an individual component and includes about 0.035% wt/wt of the composition. In one embodiment, the compositions contain about 20 μg of ethinyl estradiol.

Typically, an excess of ethinyl estradiol is utilized, and desirably a 5% excess, over the amount of ethinyl estradiol that is required for the composition. In another embodiment, the compositions contain about 21 μg of ethinyl estradiol.

Ethinyl estradiol can also be added in combination with other excipients, and desirably as a mixture with anhydrous lactose. In one embodiment, the source of the ethinyl estradiol is a triturate which contains 2% ethinyl estradiol in anhydrous lactose, whereby the ethinyl estradiol includes about 2% wt/wt of the triturate in anhydrous lactose. The term "triturate", as used herein, refers to a composition containing fine particles and/or powder. In one example, the composition contains the ethinyl estradiol 2% triturate in lactose in an amount of about 1 to about 2% wt/wt of the composition. In another example, the composition contains about ethinyl estradiol 2% triturate in lactose at an amount of about 1.75% wt/wt of the composition. This amount may be varied, depending upon the amount of ethinyl estradiol to be delivered to a patient.

The composition can also include microcrystalline cellulose. Typically, the microcrystalline cellulose includes about 30 to about 60% wt/wt of the composition. In one example, MCC includes about 30 to about 56% wt/wt of the composition. In a further example, MCC includes about 54% wt/wt of the composition. In another example, MCC includes about 54.5% wt/wt of the composition. In a further example, MCC includes about 54.4% wt/wt of the composition. In still another example, MCC includes about 54.3% wt/wt of the composition.

Anhydrous lactose can also be included in the compositions described herein. Typically, the anhydrous lactose includes about 30 to about 56% wt/wt of the composition. In one example, anhydrous lactose includes about 37% wt/wt of the composition. In a further example, anhydrous lactose includes about 38% wt/wt of the composition. In another example, anhydrous lactose includes about 39% of the composition. In a still further example, anhydrous lactose includes about 37.3% wt/wt of the composition. In yet a further example, anhydrous lactose includes about 37.2% wt/wt of the composition. In still another example, anhydrous lactose includes about 37.15% wt/wt of the composition. In a further example, anhydrous lactose includes about 38.9% wt/wt of the composition. In yet another example, anhydrous lactose includes about 38.8% wt/wt of the composition.

The compositions can further include croscarmellose sodium. Typically, croscarmellose sodium includes about 2 to about 6% wt/wt of the composition. In one example, croscarmellose sodium includes about 6% wt/wt of the composition.

Magnesium stearate can also be included in the compositions. Typically, magnesium stearate includes about 0.25 to about 0.5% wt/wt of the composition. In one example, magnesium stearate includes about 0.25% wt/wt of the composition.

In one embodiment, a composition includes about 0.175% wt/wt of micronized tanaproget, or a pharmaceutically acceptable salt thereof, about 0.035% wt/wt of ethinyl estradiol, about 54.5% wt/wt of microcrystalline cellulose, about 37.3% wt/wt of anhydrous lactose, about 6% wt/wt of croscarmellose sodium, and about 0.25% wt/wt of magnesium stearate.

In another embodiment, a composition includes about 0.35% wt/wt of micronized tanaproget, or a pharmaceutically acceptable salt thereof, about 0.035% wt/wt of ethinyl estradiol, about 54.4% wt/wt of microcrystalline cellulose, about 37.2% wt/wt of anhydrous lactose, about 6% wt/wt of croscarmellose sodium, and about 0.25% wt/wt of magnesium stearate.

In a further embodiment, a composition includes about 0.525% wt/wt of micronized tanaproget, or a pharmaceutically acceptable salt thereof, about 0.035% wt/wt of ethinyl estradiol, about 54.3% wt/wt of microcrystalline cellulose, about 37.15% wt/wt/ of anhydrous lactose, about 6% wt/wt of croscarmellose sodium, and about 0.25% wt/wt of magnesium stearate.

In still another embodiment, a composition includes about 0.525% wt/wt of micronized tanaproget, or a pharmaceutically acceptable salt thereof, about 0.035% wt/wt of ethinyl estradiol, about 54.5% wt/wt of MCC, about 39% wt/wt of anhydrous lactose, about 6% wt/wt of croscarmellose sodium, and about 0.25% wt/wt of magnesium stearate.

In yet a further embodiment, a composition includes about 0.35% wt/wt of micronized tanaproget, about 0.035% wt/wt of ethinyl estradiol, about 54.4% wt/wt of MCC, about 39.0% wt/wt of anhydrous lactose, about 6% wt/wt of croscarmellose sodium, and about 0.25% wt/wt of magnesium stearate.

In still another embodiment, a composition includes about 0.5250% wt/wt of micronized tanaproget, about 0.035% wt/wt of ethinyl estradiol, about 54.3% wt/wt of MCC, about 38.9% wt/wt of anhydrous lactose, about 6% wt/wt of croscarmellose sodium, and about 0.25% wt/wt of magnesium stearate.

Without limitation as to the method of preparation of a composition described herein, an example of a suitable micronized tanaproget composition is provided in Table 1.

TABLE 1

| Component | % wt/wt |
|---|---|
| Micronized Tanaproget | 0.1750 |
| Ethinyl Estradiol (EE) 2% Triturate in Anhydrous Lactose | 1.75 |
| MCC | 54.5037 |
| Lactose Anhydrous | 37.3213 |
| Croscarmellose Sodium | 6.00 |
| Magnesium stearate | 0.25 |

Another example of a suitable micronized tanaproget composition is provided in Table 2.

TABLE 2

| Component | % wt/wt |
|---|---|
| Micronized Tanaproget | 0.35 |
| Ethinyl Estradiol 2% Triturate in Anhydrous Lactose | 1.75 |
| MCC | 54.4120 |
| Anhydrous Lactose | 37.238 |
| Croscarmellose Sodium | 6.00 |
| Magnesium Stearate | 0.25 |

A further example of a suitable micronized tanaproget composition is provided in Table 3.

TABLE 3

| Component | % wt/wt |
|---|---|
| Micronized Tanaproget | 0.5250 |
| Ethinyl Estradiol 2% Triturate in Anhydrous Lactose | 1.75 |
| MCC | 54.3203 |
| Anhydrous Lactose | 37.1547 |
| Croscarmellose Sodium | 6.00 |
| Magnesium Stearate | 0.25 |

Still another example of a suitable micronized tanaproget composition is provided in Table 4.

TABLE 4

| Component | % wt/wt |
|---|---|
| Micronized Tanaproget | 0.1750 |
| Ethinyl Estradiol | 0.035 |
| MCC | 54.5037 |
| Lactose Anhydrous | 39.0363 |
| Croscarmellose Sodium | 6.00 |
| Magnesium stearate | 0.25 |

Yet a further example of a suitable micronized tanaproget composition is provided in Table 5.

TABLE 5

| Component | % wt/wt |
|---|---|
| Micronized Tanaproget | 0.35 |
| Ethinyl Estradiol | 0.035 |
| MCC | 54.4120 |
| Anhydrous Lactose | 38.953 |
| Croscarmellose Sodium | 6.00 |
| Magnesium Stearate | 0.25 |

In still another example of a suitable micronized tanaproget composition is provided in Table 6.

TABLE 6

| Component | % wt/wt |
|---|---|
| Micronized Tanaproget | 0.5250 |
| Ethinyl Estradiol | 0.035 |
| MCC | 54.3203 |
| Anhydrous Lactose | 38.8697 |
| Croscarmellose Sodium | 6.00 |
| Magnesium Stearate | 0.25 |

The compositions are typically prepared by combining micronized tanaproget, or a pharmaceutically acceptable salt thereof, ethinyl estradiol, MCC, croscarmellose sodium, anhydrous lactose, and magnesium stearate and mixing or granulating the mixture. Desirably, the compositions are prepared by dry mixing or granulating the components therein using techniques such as roller compaction, slugging, or a combination thereof to form a dry granulation The term "roller compaction" as used herein refers to a process by which two or more solid materials are compacted between two rotating rolls, desirably, counter-rotating rolls, to form solid ribbons. These ribbons are then subject to further steps including milling to form a composition.

The term "slugging" as used herein refers to a process by which two or more solid materials are compressed on a press, typically using presses that are larger than those presses utilized to prepare large tablets. These tablets are then subject to further steps including milling to form a composition.

The components can also be in extragranular or intragranular forms, as determined by one of skill in the art and as determined by the requirements of the process.

In addition, a variety of apparatuses can be utilized to perform the process described herein and includes bags of small, medium, and large sizes, screens of varying sizes, and blenders, among others.

The process can also include compacting or milling the composition, typically using compactors and mills selected by one of skill in the art. The milling step is typically performed on particles of varying sizes, i.e., large particles, powders, and fine powders to obtain a preferential and more uniform particle size. The milling can include several separating, recycling, and screening steps to obtain the desired particle sizes.

The compositions desirably contain particles of an optimal size to permit dissolution of the composition, and more desirably, the particles are less than or equal to about 100 μm. The sizes of the particles of the composition are typically measured by passing the solid composition through screens of varying sizes. In one embodiment, about 8% of the particles are greater than or equal to about 350 μm. In another embodiment, about 28% of the particles are greater than or equal to about 180 μm. In a further embodiment, about 34% of the particles are greater than or equal to about 150 μm. In still another embodiment, about 39% of the particles are greater than about 125 μm. In yet another embodiment, about 49% of the particles are greater than about 89 μm. In a further embodiment, about 64% of the particles are greater than about 75 μm. In still another embodiment, about 90% of the particles are greater than about 45 μm.

If the particles of the compositions are larger than the optimal size and if the same have not yet been encapsulated in a capsule, the same can be subject to further milling and screening steps, among others, to reduce the particle size.

The process typically includes compressing the composition into a form suitable for oral administration and is typically a tablet or caplet. When compressed into a tablet or caplet, one of skill in the art would readily be able to select a suitable tablet press for use herein. However, one example of such a press includes the Stokes® B2 Tablet Press, among others.

In one embodiment, the tablet prepared as described herein is encapsulated in a capsule. Desirably, the capsule is a hydroxypropyl methylcellulose or hypromellose capsule. The capsule can be optionally sealed with the tablet therein or a filler can be added to the capsule containing tablet. Typically, the filler includes MCC, croscarmellose sodium, and magnesium stearate. Desirably, the tablet is placed in the capsule prior to adding the filler. In one example, a tablet containing 0.1 mg of tanaproget and 20 µg of ethinyl estradiol is encapsulated in a capsule. In another example, a tablet containing 0.2 mg of tanaproget and 20 µg of ethinyl estradiol is encapsulated in a capsule. In a further example, a tablet containing 0.3 mg of tanaproget and 20 µg of ethinyl estradiol is encapsulated in a capsule.

In another embodiment, the tablets prepared as described herein are utilized without encapsulation. In one example, a tablet contains 0.1 mg of tanaproget and 20 µg of ethinyl estradiol is encapsulated in a capsule. In another example, a tablet contains 0.2 mg of tanaproget and 20 µg of ethinyl estradiol is encapsulated in a capsule. In a further example, a tablet contains 0.3 mg of tanaproget and 20 µg of ethinyl estradiol is encapsulated in a capsule.

Optionally, the tablets are film-coated. Suitable film-coatings are known to those of skill in the art. For example, the film-coating can be selected from among suitable polymers such as hydroxypropylmethylcellulose, ethyl cellulose, polyvinyl alcohol, and combinations thereof. Other suitable film-coatings can be readily selected by one of skill in the art. Typically, the tablet is coated with an Opadry® seal coat. Where applied, the weight percent of the film coat is generally in the range of 2% wt/wt to 6% wt/wt of the tablet.

When prepared as described herein, the tablets, capsules, or tablets-in-capsules containing a composition release about 94 to about 100% of tanaproget after about 15 minutes.

B. Stability of the Compositions

The compositions described herein are stable over a period of about 1 month for samples stored at varying temperatures and humidities. The term stable as used herein refers to the compositions which degrade less than about 1%. Typically, it is the tanaproget that degrades in the composition. Desirably, the composition is stable at about 20° C./50% relative humidity to about 45° C./75% relative humidity and at temperatures up to about 25° C.

In one embodiment, the compositions are stored at reduced temperatures, and, desirably, at temperatures of about 5° C. It is also desirable that the compositions be stored in the absence of water, air, and moisture.

In another embodiment, the compositions are stored at room temperature. Typically, a stabilizer such as cysteine, sodium thiosulfate, or a combination thereof is added to the composition in order to maintain its stability at room temperature.

C. Additional Components of the Compositions

Other suitable components can be added to the compositions, provided that the same is not already present, and will be readily apparent to one of skill in the art. Typically, the additional components are inert and do not interfere with the function of the required components of the compositions. The compositions can thereby further include other adjuvants, syrups, elixirs, diluents, excipients, binders, lubricants, surfactants, granulating agents, disintegrating agents, emollients, metal chelators, pH adjustors, surfactants, fillers, disintegrants, and combinations thereof, among others.

Adjuvants can include, without limitation, flavoring agents, coloring agents, preservatives, and supplemental antioxidants, which can include vitamin E, ascorbic acid, butylated hydroxytoluene (BHT), butylated hydroxyanisole (BHA), cysteine, and sodium thiosulfate.

Binders can include, without limitation, povidone, cellulose, methylcellulose, hydroxymethylcellulose, carboxymethylcellulose calcium, carboxymethylcellulose sodium, hydroxypropylcellulose, hydroxypropylmethylcellulose phthalate, noncrystalline cellulose, polypropylpyrrolidone, polyvinylpyrrolidone (povidone, PVP), gelatin, gum arabic and acacia, polyethylene glycols, starch, sugars such as sucrose, kaolin, dextrose, and lactose, cholesterol, tragacanth, stearic acid, gelatin, casein, lecithin (phosphatides), cetostearyl alcohol, cetyl alcohol, cetyl esters wax, dextrates, dextrin, glyceryl monooleate, glyceryl monostearate, glyceryl palmitostearate, polyoxyethylene alkyl ethers, polyoxyethylene castor oil derivatives, polyoxyethylene stearates, polyvinyl alcohol, and gelatin, among others. In one embodiment, the binder is povidone.

Lubricants can include light anhydrous silicic acid, talc, stearic acid, sodium lauryl sulfate, magnesium stearate and sodium stearyl fumarate, among others. In one embodiment, the lubricant is magnesium stearate.

Excipients can include, without limitation, silicon dioxide, starch, calcium carbonate, pectin, and crospovidone (polyplasdone), among others.

Disintegrating agents or disintegrants can include starch, carboxymethylcellulose, substituted hydroxypropylcellulose, sodium bicarbonate, calcium phosphate, calcium citrate, sodium starch glycolate, pregelatinized starch or crospovidone, among others.

Emollients can include, without limitation, stearyl alcohol, mink oil, cetyl alcohol, oleyl alcohol, isopropyl laurate, polyethylene glycol, olive oil, petroleum jelly, palmitic acid, oleic acid, and myristyl myristate.

Surfactants can include polysorbates, sorbitan esters, poloxamer, or sodium lauryl sulfate. In one embodiment, the surfactant is sodium lauryl sulfate.

Metal chelators can include physiologically acceptable chelating agents including edetic acid, malic acid, or fumaric acid. In one embodiment, the metal chelator is edetic acid.

pH adjusters can also be utilized to adjust the pH of a solution containing tanaproget to about 4 to about 6. In one embodiment, the pH of a solution containing tanaproget is adjusted to a pH of about 4.6. pH adjustors can include physiologically acceptable agents including citric acid, ascorbic acid, fumaric acid, or malic acid, and salts thereof. In one embodiment, the pH adjuster is citric acid.

Additional fillers that can be used in the compositions include mannitol, calcium phosphate, pregelatinized starch, or sucrose.

D. Methods of Using the Compositions

Further provided are methods of delivering tanaproget to a patient, where the method includes administering a micronized tanaproget dosing unit.

The dosage requirements of tanaproget may vary based on the severity of the symptoms presented and the particular subject being treated. Treatment can be initiated with small dosages less than the optimum dose of tanaproget. Thereafter the dosage is increased until the optimum effect under the circumstances is reached. Precise dosages will be determined by the administering physician based on experience with the individual subject treated. In general, the compositions are most desirably administered at a concentration that will generally afford effective results without causing any unacceptable harmful or deleterious side effects. For example, an effective amount of micronized tanaproget is generally, e.g., about 100 to about 300 μg, about 100 μg, about 200 μg, or about 300 μg.

These compositions containing micronized tanaproget are therefore useful in contraception and hormone replacement therapy. The compositions are also useful in contraception and the treatment and/or prevention of uterine myometrial fibroids, benign prostatic hypertrophy, benign and malignant neoplastic disease, dysfunctional bleeding, uterine leiomyomata, endometriosis, polycystic ovary syndrome, and carcinomas and adenocarcinomas of the pituitary, endometrium, kidney, ovary, breast, colon, and prostate and other hormone-dependent tumors. Additional uses of the compositions include stimulation of food intake.

The compositions are formed into a suitable dosing unit for delivery to a patient. Suitable dosing units include oral dosing units, such as a directly compressible tablets, caplets, capsules, powders, suspensions, microcapsules, dispersible powders, granules, suspensions, syrups, elixirs, and aerosols. Desirably, the compositions are compressed into a tablet or caplet, which is optionally added to a capsule, or the compositions are added directly to a capsule. The compositions can also be formulated for delivery by other suitable routes. These dosing units are readily prepared using the methods described herein and those known to those of skill in the art.

Solid forms, including tablets, caplets, and capsules containing micronized tanaproget can be formed by dry blending tanaproget with the components described above. In one embodiment, the capsules include hydroxypropyl methylcellulose, hypromellose capsule, or a hard shell gelatin capsule. The tablets or caplets that contain tanaproget are optionally film-coated. Suitable film-coatings are known to those of skill in the art. For example, the film-coating can be selected from among polymers such as hydroxypropylmethylcellulose, ethyl cellulose, polyvinyl alcohol, and combinations thereof.

A pharmaceutically effective amount of tanaproget can vary depending on the components of the composition, mode of delivery, severity of the condition being treated, the patient's age and weight, and any other active ingredients used in the composition. The dosing regimen can also be adjusted to provide the optimal therapeutic response. Several divided doses can be delivered daily, e.g., in divided doses 2 to 4 times a day, or a single dose can be delivered. The dose can however be proportionally reduced or increased as indicated by the exigencies of the therapeutic situation. In one embodiment, the delivery is on a daily, weekly, or monthly basis. In another embodiment, the delivery is on a daily delivery. However, daily dosages can be lowered or raised based on the periodic delivery.

It is contemplated that when the compositions are used for contraception or hormone replacement therapy, they can be administered in conjunction with one or more other progesterone receptor agonists, estrogen receptor agonists, progesterone receptor antagonists, and selective estrogen receptor modulators, among others.

When utilized for treating neoplastic disease, carcinomas, and adenocarcinomas, they can be administered in conjunction with one or more chemotherapeutic agents which can readily be selected by one of skill in the art.

E. Kits

Also provided are kits or packages containing tablets, caplets, or capsules containing micronized tanaproget and ethinyl estradiol. The kits can include tablets, caplets, or capsules containing tanaproget and ethinyl estradiol and a carrier suitable for administration to a mammalian subject as discussed above. Typically, the tablets, caplets, or capsules are packaged in blister packs, and desirably Ultrx™ 2000 blister packs The kits or packages containing the compositions are designed for use in the regimens described herein. These kits are desirably designed for daily oral delivery over 21-day, 28-day, 30-day, or 31-day cycles, among others, and more desirably for one oral delivery per day. When the compositions are to be delivered continuously, a package or kit can include the composition in each tablet or caplet. When the compositions of are to be delivered with periodic discontinuation, a package or kit can include placebos on those days when the composition is not delivered.

Additional components may be co-administered with the compositions and include antiprogestins, estrogens, and selective estrogen receptor modulators, among others.

The kits are also desirably organized to indicate a single oral formulation or combination of oral formulations to be taken on each day of the cycle, desirably including oral tablets or caplets to be taken on each of the days specified, and more desirably one oral tablet or caplet will contain each of the combined daily dosages indicated.

In one embodiment, a kit can include a single phase of a daily dosage of the composition over a 21-day, 28-day, 30-day, or 31-day cycle. Alternatively, a kit can include a single phase of a daily dosage of the composition over the first 21 days of a 28-day, 30-day, or 31-day cycle. A kit can also include a single phase of a daily dosage of the composition over the first 28 days of a 30-day or 31-day cycle.

In a further embodiment, a kit can include a single combined phase of a daily dosage of the composition and an antiprogestin over a 21-day, 28-day, 30-day, or 31-day cycle. Alternatively, a kit can include a single combined phase of a daily dosage of the composition and an antiprogestin over the first 21 days of a 28-day, 30-day, or 31-day cycle. A kit can also include a single combined phase of a daily dosage of the composition and an antiprogestin over the first 28 days of a 30-day or 31-day cycle.

In another embodiment, a 28-day kit can include a first phase of from 14 to 28 daily dosage units of the composition; and a second phase of from 0 to 7 daily dosage units of an orally and pharmaceutically acceptable placebo, wherein the total number of the daily dosage units is 28.

In yet a further embodiment, a 28-day kit can include a first phase of from 14 to 21 daily dosage units of the composition; a second phase of from 0 to 7 daily dosage units of an orally and pharmaceutically acceptable placebo.

In another embodiment, a 28-day kit can include a first phase of from 18 to 21 daily dosage units of the composition; a second phase of from 0 to 7 daily dose units of a pharmaceutically acceptable placebo.

In still a further embodiment, a 28-day kit can include a first phase of 14 daily dosage units of the composition; and a third phase of 14 daily units of an orally and pharmaceutically acceptable placebo.

In yet another embodiment, a 28-day kit can include a first phase of 17 daily dosage units of the composition; and a third phase of 11 daily units of an orally and pharmaceutically acceptable placebo.

In yet a further embodiment, a 28-day kit can include a first phase of 21 daily dosage units of the composition; and a third phase of 7 daily units of an orally and pharmaceutically acceptable placebo.

Desirably, the daily dosage of tanaproget remains fixed in each particular phase in which it is delivered. It is further preferable that the daily dose units described are to be delivered in the order described, with the first phase followed in order by the second and third phases. To help facilitate compliance with each regimen, it is also preferred that the kits contain the placebo described for the final days of the cycle.

A number of packages or kits are known in the art for the use in dispensing pharmaceutical agents for oral use. Desirably, the package has indicators for each day of the 28-day cycle, and more desirably is a labeled blister package, dial dispenser package, or bottle.

The kit can further contain instructions for administering the tanaproget composition.

Also provided is a product containing micronized tanaproget, or a pharmaceutically acceptable salt thereof, and ethinyl estradiol as a combined preparation for simultaneous, separate or sequential use in the provision of contraception to a female of child bearing age or the provision of hormone replacement therapy to a female in need thereof.

The following examples are provided to illustrate the invention and do not limit the scope thereof. One skilled in the art will appreciate that although specific reagents and conditions are outlined in the following examples, modifications can be made which are meant to be encompassed by the spirit and scope of the invention.

EXAMPLES

Example 1

Compositions Containing Micronized Tanaproget and Ethinyl Estradiol

The compositions for this example were manufactured using the following protocol and using the components of Table 7.

TABLE 7

| Component | Function |
| --- | --- |
| Tanaproget (micronized) | Active ingredient |
| Ethinyl Estradiol (EE) 2% Triturate in Lactose | Active ingredient |
| Microcrystalline Cellulose | Filler, Granulation aid, Disintegrant |
| Croscarmellose Sodium | Disintegrant |
| Anhydrous Lactose | Filler |
| Magnesium Stearate | Lubricant |
| HPMC Capsule, #1 Reddish Brown | Capsule shell |

MCC and anhydrous lactose were passed through a 30 mesh hand screen, transferred to a PK-Blender equipped with intensifier bar (pin bar), and blend for 1 minute without intensifier bar activated. A second portion of MCC and anhydrous lactose was passed through a #30 mesh hand screen into a suitable size plastic bag and blend for 1 minute. A third portion of MCC was passed through #30 mesh screen into a smaller plastic bag and the bag was shaken for 15 seconds. Tanaproget was added to the bag containing the third portion of MCC and blend for 1 minute. A third portion of anhydrous lactose was passed through a #30 mesh hand screen into the bag containing MCC and tanaproget and blend for 1 minute. The blended material was then passed through a #30 mesh hand screen into the larger bag containing the second portion of MCC and anhydrous lactose. The emptied bag was rinsed twice by mixing portion four and five of MCC and anhydrous lactose in the bag for 1 minute. The rinses were passed through the #30 mesh screen that was used to screen the tanaproget and was transferred into the larger bag containing tanaproget and the third portion of MCC and anhydrous lactose. A sixth portion of MCC and anhydrous lactose was passed through the #30 mesh hand screen that was used for the two rinses and was transferred into the plastic bag containing tanaproget and the third portions of MCC and anhydrous lactose. The bag blended to form a pre-blend. The pre-blend was transferred to the PK-Blender containing the first portions of MCC and anhydrous lactose. The emptied bag that contained the preblend was rinsed twice with portions seven and eight of MCC and anhydrous lactose that were passed through a #30 mesh hand screen into the bag shaken for 2 minutes. The rinses were transferred into the PK-blender.

A ninth portion of MCC and anhydrous lactose was passed through a #30 mesh hand screen into a plastic bag and the material was blend. Ethinyl estradiol 2.0% Triturate was passed through a #30 mesh screen into the plastic bag that had contained the ninth portion of MCC and anhydrous lactose and mixed. A tenth portion of MCC and anhydrous lactose was passed through a #30 mesh hand screen, transferred to the same plastic bag containing the ethinyl estradiol together with the ninth portions of MCC and anhydrous lactose, and the materials were mixed. An eleventh portion of MCC and anhydrous lactose were passed through a #30 mesh hand screen, transferred to the plastic bag containing the ethinyl estradiol, the material mixed, and was transferred to the PK-blender. Croscarmellose sodium was passed through #30 mesh hand screen directly into the plastic bag that contained the eleventh portion of MCC and anhydrous lactose. A twelve portion of MCC and anhydrous lactose were passed through a #30 mesh hand screen directly into the plastic bag containing the croscarmellose sodium, the bag was shaken, and the shaken material was transferred to the PK-Blender. A thirteenth portion of MCC and anhydrous lactose was passed through a #30 mesh hand screen directly to the plastic bag that had contained the twelve portion of MCC/anhydrous lactose/croscarmellose sodium, was shaken, and was transferred to the PK-Blender. Fourteenth portions of MCC and anhydrous lactose were passed through #30 mesh hand screen, transferred to the PK-Blender, and the material blend.

An intra-granular portion of magnesium stearate was passed through #30 mesh hand screen into a plastic bag, the screen was rinsed with approximately equal portion from the blend from the blender, and this pre-blend was blended. The pre-blend containing the intra-granular portion of magnesium stearate was transferred to the PK Blender and mixed. The blend was discharged from the PK Blender into a double poly-lined container. If not utilized immediately, the blend was stored under reduced temperatures of about 2 to about 8° C., in the absence of light and moisture using two desiccant bags between the two poly bags.

The tanaproget blend was compacted into ribbons using a roller compactor. The compacted ribbons were milled using a FitzMill, Model D through a #33 plate, low speed and knives forward. The milled material was sieved using a #30 mesh screen and the material on top of the screen and plate of the Fitz-Mill were collected. The materials that passed through the #30 mesh screen were then passed through a #120 mesh screen. The material retained on the #120 mesh screen was stored in a plastic bag. The powder that passed through the #120 mesh screen was compacted using the roller compactor, the compacted ribbons were milled using Fitz-Mill Model D through a #33 plate at low speed and knives forward. The milled material was passed through a #30 mesh screen and the material retained on the #30 mesh screen was combined with the milled material retained on the plate of the Fitz-Mill. All of the material that retained on top of the screen and plate of the Fitz-mill was collected, hand milled using a mortar and pestle, and passed through a #30 mesh screen. All of the materials that passed through the #30 mesh screens were combined and half of this combined material was transferred to a PK-Blender.

An extragranular portion of croscarmellose sodium was passed through a #30 mesh screen into a plastic bag, the screen was rinsed with a portion of the material that had passed through the #30 mesh screens and transferred to the bag, the blend in the bag mixed, and the blended material transferred to the PK-Blender. The remaining portion of the material that passed through the #30 mesh screens was transferred to the PK-Blender and the material mixed. An extragranular portion of magnesium stearate was passed through a #30 mesh screen into a plastic bag, the screen rinsed with a portion of the material from the blender, and the bag blend to form a pre-mix. The premix was transferred to the PK-Blender and blend for 2 min. The blended pre-mix was discharged from the PK-blender into a double poly-lined container(s) and stored under reduced temperatures of about 2 to about 8° C., in the absence of light and moisture using desiccants between the two poly bags. See, Table 8 for the total amounts of the components utilized in the composition.

MCC and croscarmellose sodium were passed through #20 mesh screen, added to a PK-blender without an intensifier bar installed, and blend for 15 minutes. Magnesium stearate was passed through #30 mesh screen and pre-mixed with a portion of the MCC/croscarmellose blend. The magnesium stearate preblend was added to the PK-blender and blend for 2 minutes to form a final placebo blend.

Using a capsule filler, formatted for size #1 capsule shell, a reddish brown opaque HPMC capsule shell was filled by placing one (1) tanaproget/EE (100 m/20 μg, 200 μg/20 μg, 300 μg/20 μg) tablet into one capsule shell body and flood filling with approximately 144 mg of the placebo blend into each capsule shell. The filled #1 reddish brown capsule body was closed using the #1 reddish brown opaque HPMC shell caps. The filled capsules were stored in poly-lined containers, in the absence of moisture, light and humidity.

Any of the final blend that was not immediately utilized for tablet encapsulation was added into a poly-lined container and stored at room temperature in the absence of moisture.

TABLE 8

| Ingredient | 100 μg Tanaproget/ 20 μg EE Tablet | | 200 μg Tanaproget/ 20 μg EE Tablet | | 300 μg Tanaproget/ 20 μg EE Tablet | |
|---|---|---|---|---|---|---|
| | Amount (mg) | % wt/wt | Amount (mg) | % wt/wt | Amount (mg) | % wt/wt |
| Micronized Tanaproget[a] | 0.105[c] | 0.1750[c] | 0.21[c] | 0.35[c] | 0.5250[c] | 0.3150[c] |
| Ethinyl Estradiol[b] | 1.05[d] | 1.75[d] | 1.05[d] | 1.75[d] | 1.75[d] | 1.05[d] |
| Microcrystalline Cellulose | 32.7022 | 54.5037 | 32.6472 | 54.4120 | 54.3203 | 32.5922 |
| Anhydrous Lactose | 22.3928 | 37.3213 | 22.3428 | 37.238 | 37.1547 | 22.2928 |
| Croscarmellose Sodium | 3.60 | 6.00 | 3.60 | 6.00 | 6.00 | 3.60 |
| Magnesium Stearate | 0.15 | 0.25 | 0.15 | 0.25 | 0.25 | 0.15 |
| Total | 60 mg | 100 | 60 mg | 100 | 60 mg | 100 |

[a]If assay is other than 100.0%, adjust the amount of input to provide the proper level of tanaproget and adjust the input of Lactose Anhydrous accordingly.
[b]If assay of EE is other than 2%, adjust the amount of input to provide the proper level of EE and adjust the lactose accordingly.
[c]Includes 5% overage of Tanaproget.
[d]Includes 5% overage of EE.

Example 2

Tablets Containing a Composition of Tanaproget and Ethinyl Estradiol

This example provides the preparation of tablets containing a composition containing tanaproget and ethinyl estradiol.

The blend from Example 1 was compressed using a Stokes® Tablet Compressor, adjusting the press as required. The tablets were stored in double polylined container with two desiccants bags placed between the two bags and stored under refrigeration at about 2-8° C., in the absence of light and moisture.

Example 3

Tablets-in-Capsules Containing a Composition of Tanaproget and Ethinyl Estradiol This example provides the preparation of tablets-in-capsules containing compositions containing tanaproget and ethinyl estradiol. This example is useful for the preparation of tablets containing 100 μg, 200 μg, and 300 μg of tanaproget. The amounts of each component are illustrated in Table 9.

TABLE 9

| Ingredient | Amount | % wt/wt |
|---|---|---|
| Tanaproget/EE Tablet | 60 mg | 1 Tablet |
| MCC | 140.4 mg | 97.5 |
| Croscarmellose Sodium | 2.88 mg | 2.0 |
| Magnesium Stearate | 0.72 mg | 0.5 |
| Size #1 HPMC Caps Opaque Brown 4P Quali-V | 77 mg | 1 Capsule |

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A product comprising an effective amount of micronized tanaproget, or a pharmaceutically acceptable salt thereof, and an effective amount of ethinyl estradiol.

2. The product according to claim 1, which comprises about 0.1% to about 1% wt/wt of tanaproget.

3. The product according to claim 2, which comprises about 0.17% to about 0.53% wt/wt of tanaproget.

4. The product according to claim 2, which comprises about 0.17% wt/wt of tanaproget.

5. The product according to claim 2, which comprises about 0.35% wt/wt of tanaproget.

6. The product according to claim 2, which comprises about 0.52% wt/wt of tanaproget.

7. The product according to claim 1, which comprises about 0.03 to about 0.05% wt/wt of ethinyl estradiol.

8. The product according to claim 7, which comprises about 0.035% wt/wt of ethinyl estradiol.

9. The product according to claim 1, wherein said ethinyl estradiol is a 2% triturate in lactose.

10. The product according to claim 9, which comprises about 1.75% of a ethinyl estradiol 2% triturate in lactose.

11. The product according to claim 1, further comprising microcrystalline cellulose, anhydrous lactose, croscarmellose sodium, and magnesium stearate.

12. The product according to claim 11, which comprises about 30 to about 56% wt/wt of microcrystalline cellulose.

13. The product according to claim 11, which comprises about 30 to about 56% wt/wt of anhydrous lactose.

14. The product according to claim 11, which comprises about 2 to about 6% wt/wt of croscarmellose sodium.

15. The product according to claim 11, which comprises about 0.25 to about 0.5% wt/wt of magnesium stearate.

16. The product according to claim 11, comprising about 0.175% wt/wt of micronized tanaproget, or a pharmaceutically acceptable salt thereof, about 0.035% wt/wt of ethinyl estradiol, about 54.5% wt/wt of microcrystalline cellulose, about 37.3% wt/wt of anhydrous lactose, about 6% wt/wt of croscarmellose sodium, and about 0.25% wt/wt of magnesium stearate.

17. The product according to claim 11, comprising about 0.35% wt/wt of micronized tanaproget, or a pharmaceutically acceptable salt thereof, about 0.035% wt/wt of ethinyl estradiol, about 54.4% wt/wt of microcrystalline cellulose, about 37.2% wt/wt of anhydrous lactose, about 6% wt/wt of croscarmellose sodium, and about 0.25% wt/wt of magnesium stearate.

18. The product according to claim 11, comprising about 0.525% wt/wt of micronized tanaproget, or a pharmaceutically acceptable salt thereof, about 0.035% wt/wt of ethinyl estradiol, about 54.3% wt/wt of microcrystalline cellulose, about 37.1% wt/wt/ of anhydrous lactose, about 6% wt/wt of croscarmellose sodium, and about 0.25% wt/wt of magnesium stearate.

19. A pharmaceutical kit comprising a daily dosage unit of said product of claim 1 and a daily dosage unit of said ethinyl estradiol.

20. The product according to claim 1, wherein said product comprises about 100 μg, 200 μg, or 300 μg of tanaproget.

21. The product according to claim 1, which comprises about 20 μg of ethinyl estradiol.

* * * * *